(12) United States Patent
Jeannin et al.

(10) Patent No.: US 7,223,287 B2
(45) Date of Patent: May 29, 2007

(54) FLEXIBLE INTRAOCULAR IMPLANT INJECTOR

(75) Inventors: Lionel Jeannin, Ancy le Vieux (FR); Guy Vitally, Villaz (FR)

(73) Assignee: Corneal Industrie, Pringy (FR)

( * ) Notice: Subject to any disclaimer, the term of this patent is extended or adjusted under 35 U.S.C. 154(b) by 757 days.

(21) Appl. No.: 10/381,549

(22) PCT Filed: Sep. 27, 2001

(86) PCT No.: PCT/FR01/02994

§ 371 (c)(1),
(2), (4) Date: Mar. 25, 2003

(87) PCT Pub. No.: WO02/26167

PCT Pub. Date: Apr. 4, 2002

(65) Prior Publication Data

US 2003/0181921 A1    Sep. 25, 2003

(30) Foreign Application Priority Data

Sep. 28, 2000 (FR) .................................. 00 12349

(51) Int. Cl.
*A61F 2/16* (2006.01)
(52) U.S. Cl. ...................... 623/6.12; 606/107
(58) Field of Classification Search .............. 606/107, 606/108, 161, 166, 167; 623/6.12, 905
See application file for complete search history.

(56) References Cited

U.S. PATENT DOCUMENTS 4,165,739 A * 8/1979 Doherty et al. ............... 604/68
5,873,879 A * 2/1999 Figueroa et al. ............ 606/107
5,876,406 A * 3/1999 Wolf et al. .................. 606/107
6,475,181 B1 * 11/2002 Potter et al. .................. 604/68

FOREIGN PATENT DOCUMENTS

| DE | 199 04 220 | 8/2000 |
|----|------------|--------|
| DE | 199 04 220 A 1 | 8/2000 |
| WO | WO 99/59668 | 11/1999 |

* cited by examiner

*Primary Examiner*—Michael J. Hayes
*Assistant Examiner*—Victor Nguyen
(74) *Attorney, Agent, or Firm*—Cohen Pontani Lieberman & Pavane LLP

(57) ABSTRACT

The invention relates to an injector device for injecting an intraocular implant into the eye of a patient, which device comprises a folding chamber for folding the optical portion of the implant, a folding member, a hollow needle for injecting the folded implant into the eye, said hollow needle opening out at a first end of said chamber, a guide channel opening out at the second end of said chamber, and a moving piston mounted in said guide channel so as to push said folded implant into said hollow needle. The piston (40) includes a cylindrical end (44) for co-operating with said implant, said end including an end face (50) that is substantially orthogonal to the length of the piston, said end face presenting an opening (52) opening out in the side wall of the end of the piston and extending over a portion only of the diameter of the piston, said end being provided with a slot (54) extending over a length l such that, together with the length of said opening, the total length is not less than the length of the haptic branch, said slot communicating with said opening and also extending over the entire diameter of the piston so as to open out at its diametral ends in the outside wall of the end of said piston.

5 Claims, 2 Drawing Sheets

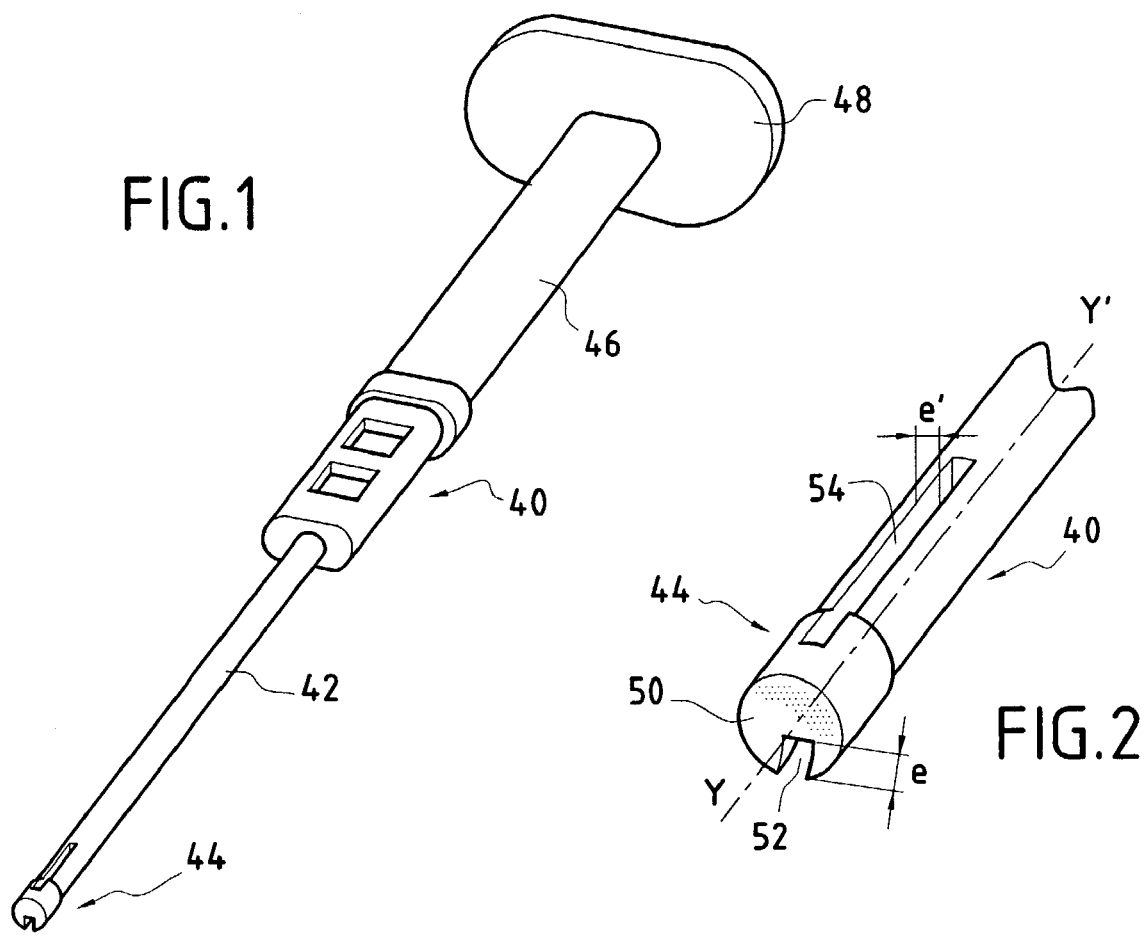
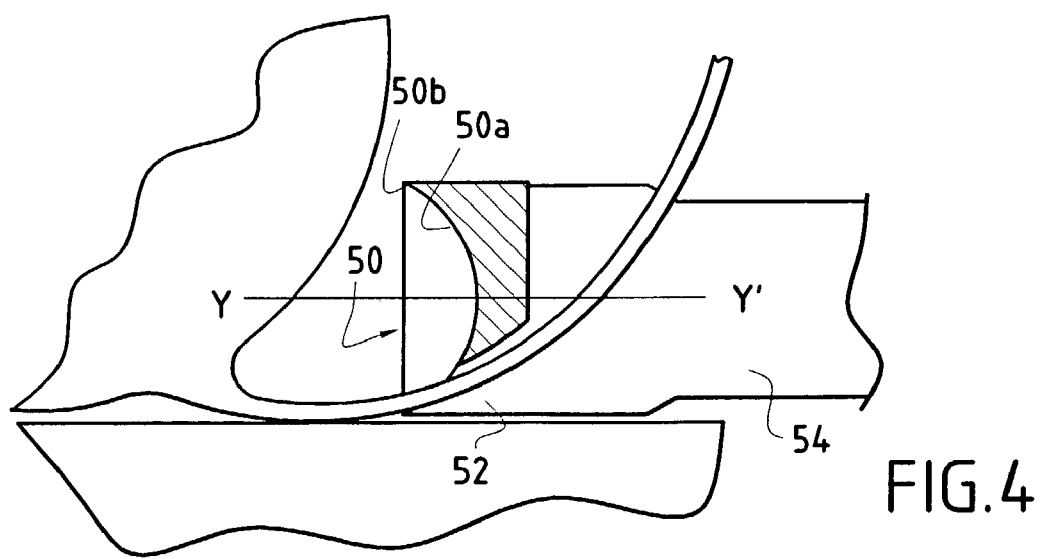

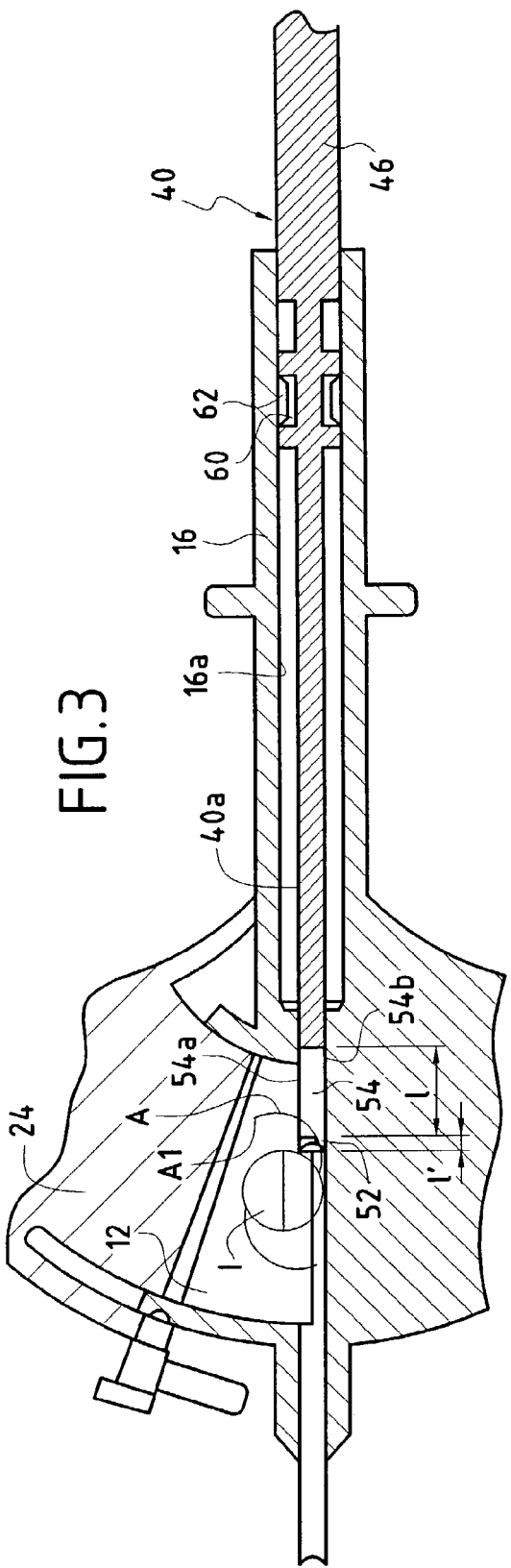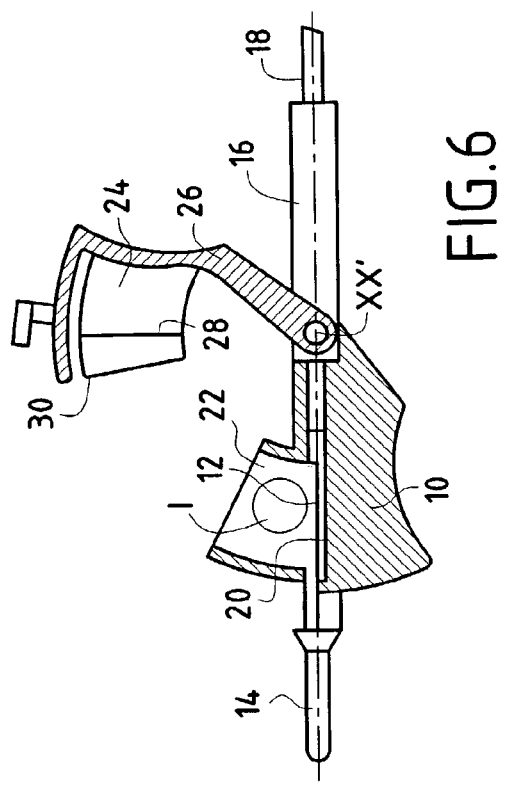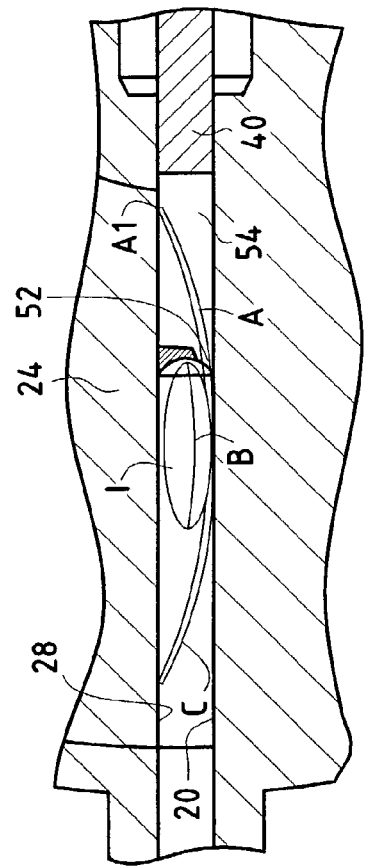

US 7,223,287 B2

FLEXIBLE INTRAOCULAR IMPLANT INJECTOR

PRIORITY CLAIM

This is a U.S. national stage of application Ser. No. PCT/FR01/02994, filed on Sep. 27, 2001. Priority is claimed from the following application: Country: France, Application No.: 00 12349, Filed: Sep. 28, 2000; the contents of which are incorporated herein by reference.

BACKGROUND OF TILE INVENTION

The present invention relates to an injector for injecting a flexible intraocular implant, and in particular it relates to a piston for such an injector.

Intraocular implants are vision-correction systems constituted by an optical portion and by a haptic portion, the haptic portion serving to hold the implant in the eye in such a manner that its optical portion presents an axis which coincides with the axis of the eye of the patient fitted with the implant. The implant is usually placed in the capsular bag of the eye once the natural lens has been removed, but it can also be put in place in the anterior chamber or in the posterior chamber of the eye of the patient.

In order to reduce the size of the incision required for putting the implant into place inside the eye, intraocular implants have been developed having an optical portion that is flexible and made of silicone or hydrophilic or hydrophobic acrylic materials. With such implants, it is possible to fold or to roll up the optical portion of the implant before inserting it into the eye, thereby enabling the total size of the implant to be reduced while it is being inserted into the eye.

The haptic portion of the implant has a purely mechanical function as explained above, and it can be presented in various ways. In some cases, the haptic portion is constituted by two haptic elements also made of a flexible material, which can therefore be rolled up or folded together with the optical portion. In other cases, the haptic portion can be constituted by two haptic branches presenting regular curvature and made of an intrinsically rigid material such as polymethylmethacrylate (PMMA), and having flexibility properties resulting from the small transverse size of the branches.

In order to assist the surgeon while the implant is being put into place in the eye, devices called intraocular-implant injectors have been developed which fulfill the dual function of rolling up or folding the implant and of inserting the folded implant into the eye by means of a hollow tube inserted through the incision made in the cornea of the eye.

SUMMARY OF THE INVENTION

FIG. 6 shows an embodiment of such an implant injector. It comprises a body 10 which defines a folding chamber 12 that is extended at one of its ends by a hollow needle 14 and at its other end by a guide channel 16 for a moving piston 18. In this embodiment, the folding chamber 12 essentially comprises a folding wall 20 of semi-cylindrical shape and a plane surface 22 for receiving the implant. The injector also comprises a moving folding-pusher 24 which, in this particular case, is mounted to pivot about an axis X–X' by means of an arm 26. The pusher 24 includes a semi-cylindrical active face 28 and a plane surface 30 parallel to the plane surface 22 of the rolling-up chamber. It should be understood that when the implant I is disposed in the rolling-up chamber on the plane surface 22 by causing the pusher 24 to pivot about its axis X–X', the semi-cylindrical active face of the pusher co-operates with one of the edges of the implant I which is sandwiched between the two semi-cylindrical surfaces 20 and 28. The movement of the pusher causes the implant to be rolled up until said implant is totally rolled up or folded inside the cylindrical volume defined by the two semi-cylindrical surfaces 20 and 28. Once the implant has been rolled up or folded, said implant can be pushed by means of the piston 18 into the hollow needle 14 for insertion into the eye of the patient.

When the haptic elements are relatively thick and made, for example, of flexible material, and are therefore folded at the same time as the optical portion, the haptic element in contact with the end of the piston 18 presents sufficient strength to ensure that the action of the piston on the haptic element does not damage the haptic element while the folded implant is being moved by the piston. In contrast, when the haptic portion is constituted by two curved branches made of rigid material and present a cross-section that is small, the action of the end of the piston 18 on the end of the haptic branch risks damaging the haptic branch and therefore making the implant itself unusable.

An object of the present invention is to provide an injector device for injecting an intraocular implant, and more particularly to provide a piston for such an injector, which piston is adapted to the case of intraocular implants including haptic branches of limited strength and can be used in an implant injector of the type described in connection with FIG. 6 or of another type in which the implant is folded or rolled up inside the injector before action of the piston enables the implant to be pushed in the folded state.

In order to achieve this object, the present invention provides an injector device for injecting an intraocular implant into the eye of a patient, which implant comprises a flexible optical portion and two haptic branches each having a first end connected to said optical portion and a second end that is free, said device comprising a folding chamber for folding the optical portion of the implant, a folding member, a hollow needle for injecting the folded implant into the eye, said hollow needle opening out at a first end of said chamber, a guide channel opening out at the second end of said chamber, and a moving piston mounted in said guide channel so as to push said folded implant into said hollow needle. The injector device is characterized in that said piston includes a cylindrical end for co-operating with said implant, said end including an end face that is substantially orthogonal to the length of the piston, said end face presenting an opening opening out in the side wall of the end of the piston and extending over a portion only of the diameter of the piston, said end being provided with a slot extending over a length l in the axial direction of the piston, said length l being such that, together with the length of said opening, the total length is not less than the length of the haptic branch, said slot communicating with the opening and also extending over the entire diameter of the piston so as to open out at its diametral ends in the outside wall of the end of said piston.

It should be understood that as a result of the presence of the opening in the end face of the piston and of the slot in the end of said piston, the haptic branch of the intraocular implant can be put in place through the opening and the slot, before the intraocular implant is folded. During the folding operation, the flexible optical portion is rolled up or folded and the haptic branch is elastically deformed so as to take on a shape that is close to a straight segment by being housed in the opening and in the slot of the piston. Thus, when the implant is to be injected into the eye of the patient, the end face of the piston acts directly on the periphery of the folded optical portion without mechanically stressing the haptic loop.

BRIEF DESCRIPTION OF THE DRAWINGS

Other characteristics and advantages of the invention appear better on reading the following description of an embodiment of the invention, given by way of non-limiting example. The description refers to the accompanying drawings, in which:

FIG. 1 is a perspective view of a piston for an implant injector of the invention;

FIG. 2 is a perspective view of the end of the rod of the piston;

FIG. 3 is a longitudinal section view of the entire implant injector fitted with the piston shown in FIG. 1;

FIG. 4 is a detail view showing the haptic branch of the intraocular implant engaged in the opening and the slot in the end of the piston;

FIG. 5 is a fragmentary longitudinal section of the implant injector showing it after the rolling-up or folding stage; and FIG. 6, already described, shows an embodiment of an intraocular-implant injector.

DETAILED DESCRIPTION OF THE PREFERRED EMBODIMENTS

FIG. 1 shows a piston 40 for an implant injector. The piston comprises a cylindrical rod 42 terminated by an end 44. The piston also comprises a thicker body 46 terminated by a surface 48 enabling the piston to be pushed into the body of the injector.

FIG. 2 shows the end 44 of the piston 40. Said end has an end face 50 which is substantially disposed in a plane that is orthogonal to the axis Y–Y' of the piston. The end face 50 of the piston is provided with an opening 52, and the end of the piston is provided with a diametral slot 54.

FIG. 3 shows an entire injector of the kind described in connection with FIG. 6, but provided with a piston 40 as shown in FIGS. 1 and 2. The injector is of the type shown in FIG. 6. However, the injector could naturally be of a different type, providing the implant is folded or rolled up in the injector, and the piston acts on an edge of the folded implant. In this figure, it can be seen that the opening 52 is disposed in a diametral plane of the piston and extends in the diametral direction over a length l that is less than the diameter of the piston, and that is preferably no more than about the radius of said piston. In a particular embodiment, the piston has a diameter equal to 2 mm, the opening 52 in the end face has a length e of 0.5 mm in the diametral direction. The slot 54 communicates with the opening 52 and extends over the entire length of the diameter of the piston. As a result, both diametral ends 54a and 54b of the slot open out to the outside wall 40a of the piston. The opening 52 presents an axial length l', and the slot 54 presents an axial length l. The lengths l' and l are determined in such a manner that their sum is not less than the length of the haptic branch A of the intraocular implant I. The sum of the lengths can be equal to 10 mm.

The opening 52 and the slot 54 preferably have the same width e' in section on planes that are orthogonal to the axis Y–Y' of the piston. Naturally, this width is greater than the thickness of the haptic branch of the implant. This width can be about 0.3 mm.

As can be seen better in FIG. 4, the end face 50 of the piston is preferably not plane, but is constituted by a spherical cap 50a of axis Y–Y', the spherical cap being concave.

This figure also shows that the diametral dimension e of the opening 52 preferably increases progressively from the end face 50 to the slot 54. This disposition makes it easier to insert the branch of the implant into the opening 52.

As a result of the fact that the opening 52 corresponds only to a fraction of the diameter of the piston, the branch of the implant remains securely held in the opening 52 and the slot 54. Furthermore, it is the periphery of the end face 50 which bears on the periphery of the optical portion of the implant.

As can be seen better in FIG. 3, the body 46 of the piston is preferably provided with temporary retention means, preferably temporary clip means 60 which can co-operate with temporary retention means, preferably temporary clip means 62 provided in the inside face 16a of the guide channel 16 of the implant injector. The temporary clip system enables the entire piston 40 to be temporarily prevented from moving in translation, in a position such that the entire slot 54 at the end of the piston is disposed inside the rolling-up chamber 12 of the intraocular-implant injector. The piston 40 is shown in this position in FIG. 3. In this position, no mechanical stress is applied to the implant or to its haptic portion. In this position of the piston, the implant can thus be stored inside the injector.

Operation of the injector shown in FIGS. 2 to 5 is described below. With the piston 40 in the position shown in FIG. 3 and held in said position by means of the temporary clip system 60, 62, the pusher 24 of the injector is fully extended, as shown in FIG. 6. The implant I is thus put in place on the plane surface 22 of the rolling-up chamber by engaging the free end A1 of the haptic branch A firstly in the opening 52, and then in the slot 54. After this operation, the implant occupies the position shown in FIG. 3, and the free end A1 of the haptic loop A projects out of the slot 54.

FIG. 5 shows an implant injector when the pusher 24 is in its final position, in which the semi-cylindrical surfaces 20 and 28 define the "rolling-up chamber", i.e. the optical portion B of the implant I is rolled up or folded, and the haptic loop A1, previously inserted into the slot 54, is subjected to stress which causes it to deform so as to bring it into a substantially rectilinear position inside the slot 54 and the opening 52, and the second haptic loop C is subjected to exactly the same deformation.

It will be understood that in order to insert the folded implant into the eye of the patient, it suffices to insert the hollow needle 14 through the incision made in the cornea of the patient. The surgeon then drives in the piston 16 causing the end face 50 of the piston to bear against the end of the rolled-up optical portion. The piston thus exerts no mechanical stress on the haptic loop A. This thrust enables the implant to be moved into the hollow needle and to be inserted into the eye, in which the intraocular implant returns to its initial shape.

It should also be emphasized that the end face 50 of the piston is preferably in the shape of a concave spherical cap. The periphery 50b of the spherical cap thus forms an obtuse angle with the inside wall of the guide channel and of the rolling-up chamber. This prevents any risk of the end of the piston pinching the inside wall of the channel or of the rolling-up chamber when the piston is driven in.

The invention claimed is:

1. An injector device for injecting an intraocular implant into the eye of a patient, said implant comprising a flexible optical portion and two haptic branches each having a first end connected to said optical portion and a second end that is free, said device comprising:
- a folding chamber for folding the optical portion of the implant, said chamber having a first and a second end,
- a folding member,
- a hollow needle for injecting the folded implant into the eye, said hollow needle opening out at said first end of said chamber,
- a guide channel having an inside wall opening out at said second end of said chamber, and
- a moving piston mounted in said guide channel so as to push said folded implant into said hollow needle, said piston having a longitudinal axis, said piston including a cylindrical end for co-operating with said implant, said end including an end face substantially orthogonal to the length of the piston and a side wall, said end face presenting an opening that opens out in said side wall of the end of the piston and extends over a portion of the diameter of said end of the piston, said portion being less than the entire diameter of said end, said end being provided with a slot extending over a length in the axial direction of the piston, said slot length being such that, together with the length of said opening, the total length is not less than the length of the haptic branch, said slot communicating with said opening and also extending over the entire diameter of said end of the piston so as to open out at its diametral ends in said outside wall of the end of said piston, said slot and said opening having substantially the same width and substantially the same diametral median plane.

2. A device according to claim 1, wherein said end face is in the shape of a concave spherical cap, having the same axis as said piston.

3. A device according to claim 1 wherein said piston and said inside wall of said guide channel include temporary retention means for holding said piston in a position such that the entire slot of the piston is in said folding chamber.

4. A device according to claim 1 wherein the dimension of said opening in the diametral direction of the piston, in said end face, is not greater than the radius of the piston.

5. A device according to claim 1 wherein the dimension of said opening in the diametral direction of the piston increases progressively from said end face to said slot.

* * * * *